United States Patent [19]

Gallagher, Jr. et al.

[11] 4,104,379

[45] Aug. 1, 1978

[54] SUBSTITUTED 1-ALKYLTHIOPHENYL-2,3,4,5-TETRAHYDRO-1H-3-BENZAZEPINE COMPOUNDS

[75] Inventors: Gregory Gallagher, Jr., Collegeville, Pa.; Francis R. Pfeiffer, Cinnaminson, N.J.; Joseph Weinstock, Phoenixville, Pa.

[73] Assignee: SmithKline Corporation, Philadelphia, Pa.

[21] Appl. No.: 760,480

[22] Filed: Jan. 19, 1977

[51] Int. Cl.$^2$ .................. A61K 31/55; C07D 223/16
[52] U.S. Cl. ........................... 424/244; 260/239 BB; 260/570.6
[58] Field of Search .................. 260/239 BB; 424/244

[56] References Cited

U.S. PATENT DOCUMENTS

| 3,393,192 | 7/1968 | Walter et al. | 260/239 BB |
| 3,483,185 | 12/1969 | Tokolics et al. | 260/239 BB |
| 4,011,319 | 3/1977 | Kaiser et al. | 424/244 |
| 4,052,506 | 10/1977 | Kaiser et al. | 424/244 |

*Primary Examiner*—Donald G. Daus
*Assistant Examiner*—D. B. Springer
*Attorney, Agent, or Firm*—William H. Edgerton

[57] ABSTRACT

A group of 1-phenyl-1H-3-benzazepines whose structures are characterized by having a functional thio containing group on the 1-phenyl moiety and which have pronounced peripheral and diminished central dopaminergic activity. This activity is manifested in an antihypertensive effect in humans. Particular species of this group include 6-chloro-7,8-dihydroxy-1-p-methylthiophenyl-2,3,4,5-tetrahydro-1H-3-benzazepine and its derivatives which have dopaminergic activity.

16 Claims, No Drawings

SUBSTITUTED 1-ALKYLTHIOPHENYL-2,3,4,5-TETRAHYDRO-1H-3-BENZAZEPINE COMPOUNDS

This invention comprises a new group of compounds which are 1-phenyl-2,3,4,5-tetrahydro-1H-3-benzazepines whose structures essentially have a functional sulfur containing group substituted on the 1-phenyl moiety. An important subgeneric group of compounds are those having structures also containing a halo or halo-containing group substituted at the 6-position of the benzazepine nucleus.

These compounds have utility as medicinally active compounds especially as diuretic and/or cardiovascular agents due to their peripheral dopaminergic activity. They demonstrate relatively less activity in animal tests which are known to predict anti-Parkinsonism activity by means of activity at central dopamine receptors than do compounds lacking the methylthio group. Generally speaking therefore they have substantial peripheral and diminished central dopaminergic activity.

The structures of the compounds of this invention are specifically identified by having a sulfur containing substituent, for example a lower alkylthio group, on the 1-phenyl of the 1-phenyltetrahydro-1H-3-benzazepine system. Exemplary of this new group of compounds are those represented by the following structural formulas:

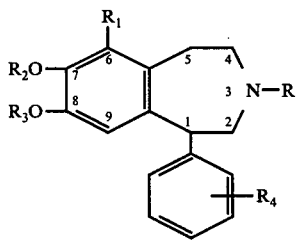

in which:
R is H, benzyl, phenethyl, carbobenzoxy, lower alkanoyl of from 1-5 carbons such as formyl, acetyl or trifluoroacetyl, lower alkyl of 1-5 carbon atoms, hydroxyethyl or lower alkenyl of 3-5 carbon atoms;
$R_1$ is hydrogen, halo such as chloro, fluoro, iodo or trifluoromethyl;
$R_2$ and $R_3$ are each hydrogen, lower alkyl of 1-5 carbon atoms, lower alkanoyl of 2-5 carbon atoms or, when taken together, methylene or ethylene; and
$R_4$ is a functional sulfur containing group such as lower alkylthio, sulfonyl or sulfinyl groups; trifluoromethylthio, sulfonyl or sulfinyl groups, or dimethylsulfonium halide ($-S(CH_3)_2X$), $R_4$ being preferably substituted at the meta and especially at the para position of the 1-phenyl moiety.

In the term, lower alkyl, as used herein straight or branched alkyl groups having 1 to 5 carbon atoms are included. Lower alkanoyl groups have 1-5 carbons substituted on N; 2-5 carbons on O. The term, X, in connection with the dimethylsulfonium group is a nontoxic, pharmaceutically acceptable anion such as the commonly used halides i.e. chloride, bromide or iodide, tosylate or mesylate. Certain of the compounds of this new series have their principal utility as intermediates such as the compounds of Formula I in which R is benzyl, phenethyl, or alkanoyl or in which $R_2$ and $R_3$ are higher alkyl, methylene or ethylene as will be evident to those skilled in the art.

$R_2O$ and $R_3O$ are preferably hydroxy radicals for maximum biological activity.

A subgeneric group of compounds within the above illustrative generic group are those of Formula I in which:
R is H or methyl.
$R_2$ and $R_3$ are the same and are hydrogen, methyl or acetyl; and
$R_4$ is methylthio, methylsulfonyl, methylsulfinyl or dimethylsulfonium bromide preferably in the meta or para position.

Individual compounds of note are those of Formula II

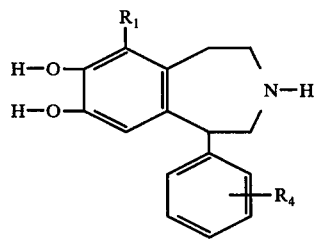

in which:
$R_1$ is chloro or hydrogen; and
$R_4$ is p-methylthio, m-methylsulfonyl or p-dimethylsulfonium bromide.

The compounds of this invention may also have a fourth nuclear substituent such as a halo, methyl, methoxy, etc. at the 9 position but these are of no particular additional advantage from the viewpoint of their biological utility. The compounds in which $R_2$ and $R_3$ form an alkylene chain such as the methylenedioxy-containing compounds at the 7,8-positions are of primary interest as intermediates as stated above. Methylenedioxy-3-benzazepines in another series are reported in U.S. Pat. No. 3,795,683.

The pharmaceutically acceptable acid addition salts having the utility of the free bases of formula I, prepared by methods well known to the art, are formed with both inorganic or organic acids, for example: maleic, fumaric, benzoic, ascorbic, pamoic, succinic, bismethylene-salicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. Similarly the quaternary salts include those prepared from organic halides such as methyl iodide, ethyl iodide, benzyl chloride and the like.

Certain 1-phenyl-2,3,4,5-tetrahydro-1H-3-benzazepines have been described in U.S. Pat. No. 3,393,192; British Patent Specification 1,118,688; and Swiss Pat. No. 555,831, including general methods of preparation. However these references disclose no lower alkylthio-substituted 1-phenyl compounds, no 6-substituted compounds of any kind and no biological advantage to specific substitution by functional sulfur containing substituents in the 1-phenyl moiety.

It will be obvious to one skilled in the art that the compounds of Formula I may be present as enantiomers which may be resolved into d or l optical isomers. Resolution of the optical isomers may be conveniently accomplished by fractional crystallization of the salts of the bases or a solid derivative thereof with optically active acids from appropriate solvents. Unless otherwise specified herein or in the claims, it is intended to include all isomers, whether separated or mixtures thereof. Where isomers are separated, the desired pharmacological activity will usually predominate in one of the isomers usually the d-isomer.

The compounds of Formula I are generally prepared from intermediates of the following formula:

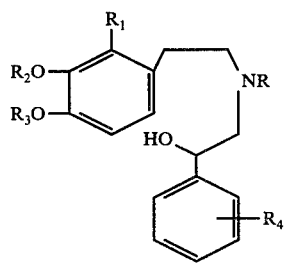

III in which R is hydrogen, lower alkyl, benzyl etc., $R_1$ is hydrogen, halo or trifluoromethyl; $R_2$ and $R_3$ are lower alkyl or together are methylene or ethylene; and $R_4$ is a chemically inert substituent of the group described above by means of an intramolecular cyclization effected by reaction with a reagent such as boron trifluoride etherate, sulfuric acid alone of mixed with suitable solvents such as trifluoroacetic acid, polyphosphoric acid, hydrobromic acid or a similar cyclizing agent as such are known to the art.

Mixed alkoxy or N-alkyl, alkenyl or benzyl substituted compounds are prepared by selecting the proper phenethylamine starting material. To obtain the benzazepine products wherein $R_2$ and $R_3$ are hydrogen most readily the corresponding methoxy substituted compounds are specifically demethylated such as using boron tribromide in a suitable solvent such as methylene chloride in the cold or at room temperature.

The phenethylamines (IV) which are used as starting materials for this method are either known or are prepared by methods described in U.S. Pat. No. 3,211,792, Chem. Abst. 80, 95398, U.S. Pat. No. 3,869,474, U.S. Pat. No. 3,804,839 or in the illustrative examples here disclosed.

The intermediates of Formula III above are conveniently prepared by heating equimolar amounts of a alkylthio substituted styrene oxide with a 3,4-dialkoxy-phenethylamine both of which are either known or prepared by methods known to the art either alone or in an inert organic solvent such as tetrahydrofuran. Preferably the heating is effected on a steam bath or at reflux temperature for from 3 to 24 hours. The required styrene oxide is conveniently prepared by reaction of the ylide derivative from sodium hydride and trimethylsulfonium iodide with the appropriately substituted benzaldehyde. The exemplary matter presented hereafter gives appropriate instructions to those skilled in the art on how to prepare starting materials as well as how to prepare the compounds of this invention.

The dialkanoyloxy derivatives such as the important 7,8-diacetoxy compounds are prepared by direct O-acylation of the 6-halo-7,8-dihydroxy-1-alkylthio, sulfinyl or sulfonylphenyl-2,3,4,5-tetrahydro-1H-3-benzazepine hydrobromides in trifluoroacetic acid at ambient temperature with the anhydride or halide. The N or 3-lower alkanoyl congeners in the dihydroxy series are prepared conveniently by N-acylating the 7,8-methylene-dioxy derivative followed by splitting the protective group with weak agents such as boron trichloride. Also direct N-alkanoylation of the dihydroxy compounds is possible under controlled conditions and quantities of reactants as known to the art. Any O-acylation may necessitate a mild hydrolysis treatment.

If during alkylation reaction the sulfonium derivative is prepared such as at the methylthio group, these may be selectively treated with an excess of chloride or bromide ion such as heating in 1N hydrobromic acid or brine.

The various 6-halo compounds may also be obtained by the oxidation of the 7,8-catechol intermediate to the quinone followed by addition of a hydrohalic acid to the quinone. The oxidized members of the thio containing phenyl substituents are readily prepared by appropriate oxidation of the thio congeners by oxidizing agents known to the art. The oxidation-addition may be controlled stepwise by the use of cyclic voltammetry methods.

The active dopaminergic compounds of this invention used herein stimulate peripheral dopamine receptors. For example, they increase renal blood flow and have as an end result a hypotensive activity. This renal vasodilator activity of the benzazepine compounds of Formula I is measured in an anesthetized dog. In this pharmacological procedure, a test compound is administered at progressively increasing (3-fold) infusion rates beginning at 0.1 mcg/kg/min up to 810 mcg/kg/min for 5 minutes each to anesthetized normotensive dogs and the following parameters are measured: renal artery blood flow, iliac artery blood flow, arterial blood pressure and heart rate. Results are reported as a percent change, increase or decrease, at time of peak response (from pre-drug controls), and for a significant effect renal blood flow (increase) and renal vascular resistance (decrease) should be approximately 10% or greater. The effect on renal vascular resistance can be calculated from any change in renal blood flow and arterial blood pressure. To confirm the mechanism of action, representative active renal vasodilator compounds are checked for blockade by bulbocapnine which is known to be a specific blocker of renal dopamine receptors. Representative compounds of Formula I, 7,8-dihydroxy-1-phenyl-2,3,4,5-tetrahydro-1H,3-benzazepine substituted in the 1-phenyl by a p-methylthio, a m-methylsulfonyl or a p-dimethylsulfonium bromide, tested by i.v. infusion as described above produced an $ED_{15}$ of 70, 132 and 40 mcg/kg respectively with little direct effect on systemic blood pressure in normotensive animals. $ED_{15}$ therefore is the cumulative dose by infusion which produces a 15% decrease in renal vascular resistance $$(R = \frac{\text{B.P. in } \frac{mm}{hg}}{\text{B.F. } \frac{ml}{min}}).$$

As a renal vasodilator in the anesthetized dog the 6-chloro 1-p-methylthiophenyl compound had an $ED_{50}$ of 60 mcg/kg per minute by infusion.

In addition to the renal vasodilator activity via a dopaminergic effect, certain benzazepine compounds of Formula I produce weak diuretic activity. Such diuretic activity is measured in the standard saline-loaded rat procedure. A test compound is administered i.p. at doses of from 10 to 40 mg/kg and the parameters measured are urine volume (hourly for three hours) plus sodium and potassium ion concentrations. For example the m-methylsulfonylphenyl containing compound showed increase sodium ion excretion and increased volume at 10 and 30 mg/kg i.v. Also conventional diuretic tests in the dog may be used. 7,8-Dihydroxy-1-p-methylthiophenyl-2,3,4,5-tetrahydro-1H-3-benzazepine hydrobromide tested in the phosphate mannitol dog produced a significant increase in natriuresis at a dose of 2 mg/kg p.o.

The benzazepine compounds of Formula I, especially in the subgeneric groups unexpectedly have diminished central dopaminergic activity as demonstrated by employing a modified standard animal pharmacological test procedure reported by Ungerstedt et al., in Brain Research 24, 1970, 485–493. This procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rat turning model. These compounds directly activate the dopamine receptors and cause contralateral rotation of the lesioned rat.

Rotational activity is defined as the ability of a compound to produce 500 contralateral rotations during a 2-hour period after administration, usually intraperitoneally. The dose corresponding to 500 contralateral rotations per two hours is obtained and assigned as the $RD_{500}$ value.

Generally speaking the new compounds of this invention have sharply diminished central dopaminergic activity but substantial peripheral dopaminergic activity than do the des-thio-congeners. For example 7,8-dihydroxy-1-(p-methylthiophenyl)-2,3,4,5-tetrahydro-1H-3-benzazepine in the described tests had an $ED_{50} = 70$ and was inactive in the turning model test at the screening dose. The m-methylsulfonyl had an $ED_{15} = 132$ and was inactive in the CNS test. The p-S$\oplus$ (CH$_3$)$_2$Br$\ominus$ had an $ED_{15} = 110$ and was inactive in the CNS test. 6-Chloro-7,8-dihydroxy-1-(p-methylthiophenyl)-2,3,4,5-tetrahydro-1H-3-benzazepine had an $ED_{15}$ of 60 and $RD_{500} = 10$, the later much less potent than that of the des-methylthio compound. Other members of this new series of compounds have less significant activities in both tests but the data presented demonstrates that the insertion of a functional thio moiety in the 1-phenyl ring of 7,8-dihydroxy-1-phenyl-3,4,5,6-tetrahydro-1H-3-benzazepine derivatives diminishes the ability of a compound to cross the blood-brain barrier thereby enhancing the specificity of action at the peripheral dopamine receptors.

The pharmaceutical compositions of this invention having dopaminergic activity are prepared in conventional dosage unit forms by incorporating a compound of Formula I, an isomer or a pharmaceutically acceptable acid addition salt thereof, with a nontoxic pharmaceutical carrier according to accepted procedures in a nontoxic amount sufficient to produce the desired pharmacodynamic activity in a subject, animal or human in need of such treatment. Preferably the compositions will contain the active ingredient in an active but nontoxic amount selected from about 15 mg to about 1000 mg of active ingredient per dosage unit but this quantity depends on the specific biological activity desired and the conditions of patient. The compositions are administered as found necessary to maintain effective dopaminergic activity usually from 1–5 times daily. Generally speaking lower doses are needed to stimulate central dopamine receptors than peripheral receptors.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier for oral administration is used the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses will be administered several times such as two or three times a day with the daily dosage regimen being selected from about 50 mg to about 2 g. When the method described above is carried out hypotensive and/or diuretic activity is produced with a minimum of side effects.

The following examples are designed solely to illustrate the preparation and use of the compounds of this invention. The temperatures are Centigrade. Other variations of these examples will be obvious to those skilled in the art.

EXAMPLE 1

Chlorine (25.6 g, 0.362 mole) was bubbled into a slurry of isovanillin (50.0 g, 0.328 mole) in 500 ml of carbon tetrachloride over a period of 25 minutes while maintaining an internal temperature of 15°–20°. Upon completion of the chlorine addition the slurry was stirred for 1 hour at room temperature; the precipitate filtered, washed with carbon tetrachloride and dried to 57.8 g (94.5% crude yield), mp: 181°–196°.

Recrystallization of 34.5 g of the crude produce from 600 ml of ethanol gave 17.3 g of white fibrous crystals, mp: 199°–203°; concentrating the mother liquors yielded a second crop of 6.3 g, mp: 196–202.5 (68% recovery for two crops).

Recrystallization of 11.4 g of crude 2-chloroisovanillin from 170 ml of acetonitrile afforded 7.4 g, mp: 200°–204.5° (65% recovery for one crop).

This compound (189.3 g) was methylated using dimethylformamide solution with potassium carbonate and dimethylsulfate to give 2-chloro-3,4-dimethoxybenzaldehyde, m.p. 69°–70°. This material (180 g) was condensed with nitromethane in acetic acid-ammonium acetate to give 2-chloro-3,4-dimethoxy-$\beta$-nitrostyrene, m.p. 88°–91° which (80 g) was reduced with lithium aluminum hydride to give 2-(2-chloro-3,4-dimethoxyphenyl)ethylamine distilling at 142°–155° at 0.5 mm.

A mixture of the ethylamine (17.4 g, 0.081 mole) and p-methylthiostyreneoxide (16.6 g, 0.081 mole) [containing about 20% mineral oil] was heated and stirred neat on a steam bath for 1½ hours. The residue was treated with 60 ml of benzene causing it to crystallize; after dilution with petroleum ether the solid was collected and recrystallized from ethanol/pet. ether to give 12.6 g (41% yield) of white N-[(2-hydroxy-2-p-thiomethylphenyl)ethyl]-N-[2-(2'-chloro-3',4'-dimethoxyphenyl)ethyl]amine, mp: 98.5°–101.5°.

A solution of 10.0 g (0.0262 mole) of N-[2-hydroxy-2-p-thiomethylphenyl)ethyl]amine, 2.2 ml of concentrated sulfuric acid and 50 ml of trifluoroacetic acid was stirred at room temperature for 2⅔ hours. The volatiles are stripped off on the rotary evaporator at 40°. Water was added to the residue which was then basified with concentrated ammonium hydroxide and extracted twice with ethyl acetate; the combined extracts were washed three times with water, dried over potassium carbonate and concentrated to a tan oil (9.3 g). The crude product was chromatographed on 200 g of silica gel eluting with chloroform containing up to 10% methanol. The purified tan oil weighed 7.9 g (83% yield) and slowly crystallized to a light yellow 6-chloro-7,8-dimethoxy-1-(p-thiomethylphenyl)-2,3,4,5-tetrahydro-1H-3-benzazepine, mp: 110°–112.5°; single spot on tlc (9:1, chloroform/methanol, silica gel).

Salts of this compound are prepared by dissolving the base in ethyl acetate and adding the desired acid or lower alkyl halide, tosylate or mesylate.

A solution of 6-chloro-7,8-dimethoxy-1-(p-thiomethylphenyl)-2,3,4,5-tetrahydro-1H-3-benzazepine (12.4 g, 0.0341 mole) in 150 ml of dry methylene chloride was cooled in an ice-methanol bath and 51.5 ml. (0.103 mole) of a 2.0 molar solution of boron tribromide in methylene chloride was added dropwise with stirring. Upon completion of the addition the cooling bath was removed and stirring continued for 3 hours. The flask was cooled in an ice bath and excess methanol was added slowly as a tan precipitate formed. The mixture was concentrated to dryness on the rotary evaporator; the residue was taken up in methanol and again concentrated. The residue was dissolved in a hot mixture of water-methanol and allowed to cool in the refrigerator overnight. The solid was filtered and air-dried to 11.0 g (78% yield) of 6-chloro-7,8-dihydroxy-1-(p-thiomethylphenyl)-2,3,4,5-tetrahydro-1H-3-benzazepine, hydrobromide, mp: 271° (decomp.); single spot on tlc (75:23:2 of ethyl acetate/methanol/ammonium hydroxide, on silica gel).

The salt is shaken in a chloroform/carbonate mixture. The organic extracts are combined, dried and evaporated to give the base.

EXAMPLE 2

To 7.7 g of 50% sodium hydride in mineral oil (0.16 mole) was added 125 ml of dry dimethylsulfoxide. The suspension was stirred under nitrogen at 65°–70° for about 80 minutes. The dark grey mixture was diluted with 100 ml of dry tetrahydrofuran, cooled in ice water and a solution of 32.7 g (0.16 mole) of trimethyl sulfonium iodide in 125 ml of dimethylsulfoxide was added over a few minutes. After stirring for an additional 3 minutes at 0°, a solution of 15.0 g (0.1 mole) of p-methylthiobenzaldehyde in 40 ml of tetrahydrofuran was added over 2 minutes. The mixture was stirred for 15 minutes at 0° and then for 1 hour at 25°, poured into 1½ liters of ice water and extracted several times with 1:1 ether-benzene. After washing well with water, the combined extract was dried over magnesium sulfate and evaporated to the crude, yellowish, syrupy epoxide. About 18 g of homoveratrylamine was added to the epoxide and the neat mixture was stirred and heated at 105° for 18 hours. The cooled reaction was diluted with 30 ml of benzene and 20 ml of ethanol, cooled and scratched to give 10.2 g (29%) of the amino alcohol, mp 105°–106.5° (from ethanol).

A mixture of 2.5 g of the amino alcohol and 45 ml of 48% hydrobromic acid was stirred at 105° for 1¼ hr. under nitrogen. The mixture was cooled, diluted with 100 ml of water, treated with activated charcoal, filtered and concentrated at 50° in vacuo. After azeotroping several times with ethanol the crystalline mass was dissolved in 200 ml of hot methanol and concentrated to incipient crystallization. The white solid was filtered and washed with a little cold methanol and then ether to give white crystals (2.3 g, 84%) of 7,8-dihydroxy-1-(p-dimethylsulfoniumphenyl)-2,3,4,5-tetrahydro-1H-3-benzazepine bromide hydrobromide as the hydrate, mp 161°–163° d.

A solution of 2.2 g of the methyl sulfonium salt in 10 ml of 48% hydrobromic acid and 40 ml of water was heated under nitrogen in an oil bath kept at 125°–130° for 2½ hours. The solvents were evaporated and the residue was evaporated several times with additional water to give a brownish solid. A crystallization from a small amount of water/acetonitrile gave the white, crystalline hydrobromide salt of 7,8-dihydroxy-1-(p-methylthiophenyl)-2,3,4,5-tetrahydro-1H-3-benzazepine, 1.3 g (74%) mp 237°–238°.

EXAMPLE 3

A solution of 17.2 g of the amino alcohol from Example 2 in 50 ml of concentrated hydrochloric acid and 100 ml of glacial acetic acid was heated in an oil bath held at 110° for 1 hour. The solution was poured into 500 ml of ice water and basified (pH > 12) with 40% sodium hydroxide solution. The whitish solid was extracted into ethyl acetate (4X) and the extracts were washed well with water, dried and concentrated to 15 g of syrupy 7,8-dimethoxy-1-(p-methylthiophenyl)-2,3,4,5-tetrahydro-1H-3-benzazepine. Tlc (9:1 CHCl$_3$/MeOH) showed one small impurity and the IR, NMR and mass spectrum were consistent with structure so the entire reaction mixture was converted to the N-carbobenzoxy derivative as follows.

The crude benzazepine was dissolved in 75 ml of acetone and diluted with 60 ml of water. Then a solution of 13. g of sodium carbonate in a minimum amount of water was added and the mixture was cooled in ice water. A solution of 11.7 g of carbobenzoxychloride in 25 ml of acetone was added at a fairly rapid rate. The suspension was stirred for 1 hour at +5°, stored overnight at +5° and then stirred for 1 hour at 25°. A large quantity of water was added and the product was extracted into ethyl acetate, washed well with brine, dried and concentrated to 19. g of yellowish, syrupy N-carbobenzoxy derivative. This was dissolved in a minimum amount of ethyl acetate, cyclohexane was added to the cloud point and then the mixture was introduced atop a column packed with 650. g of silica gel (60–230 mesh) (which had been prepared with cyclohexane). Elution with a cyclohexane-ethyl acetate gradient (1 liter of 4:1, 3 liters of 3:1 and 2 liters of 2½:1 of cyclohexane-ethyl acetate) gave about 17 g of nearly homogeneous carbobenzoxy compound as a foam. Mass spectrum and the NMR agreed with structure.

A solution of 6.0 of this derivative, 150. ml of acetic acid and 40 ml of 30% hydrogen peroxide was stirred at room temperature overnight. The mixture was poured into a large volume of water, a white solid was separated by filtration which was washed well with water, 5% sodium bicarbonate and water again. The tlc showed that all the starting material was consumed. The product was chromatographed over silica gel by eluting with 2:1 to 1:1 cyclohexane in ethyl acetate. Most of the homogeneous product came over in the 1:1 cuts to give about 5 g of the N-carbobenzoxy methyl sulfone as a low melting solid. The NMR, IR and mass spectral data verified the structure.

In 100 ml of dry methylene chloride was dissolved 3.5 g of the sulfone. The solution was cooled to −20° and a solution of 7 g of boron tribromide in 35 ml of dry methylene chloride was added dropwise. The mixture was stirred in the cold for ½ hour, then at 25° for 1½ hours. The white suspension was recooled in ice and excess methanol was added cautiously. The white suspension was concentrated and azeotroped several times with methanol. The crystalline residue was digested on the steam bath in a little water, cooled and filtered to give 2.5 g of white, crystalline product. This was dissolved in 200 ml of 1:1 water-methanol filtered and concentrated to about 50–75 ml in a nitrogen stream on a steam bath. Cooling and scratching gave 2.3 g of white crystalline 7,8-dihydroxy-1-(p-methyl-sulfonyl-phenyl)-2,3,4,5-tetrahydro-1H-3-benzazepine hydrobromide, mp > 310°.

EXAMPLE 4

A solution of formaldoxime was prepared by heating a mixture of 46 g of paraformaldehyde, 105.2 g (1.51 mole) of hydroxylamine hydrochloride and 640 ml of water on the steam-bath for 15 minutes. This clear solution was treated with 204 g (1.50 moles) of sodium acetate trihydrate and heating was continued for 20 minutes.

A solution of diazonium salt was prepared as follows: A mixture of 139.2 g (1.0 mole) of m-methylthioaniline, 300 ml of water and 228 ml of conc. hydrochloric acid was diluted with 400 g of ice. To this slurry was added a solution of 70 g (1.01 moles) of sodium nitrite in 100 ml of water drop-wise over 30 minutes at 0°–3°. The dark red mixture was stirred an additional 15 minutes, filtered through glass wool (vacuum) and carefully neutralized to congo red with a solution of 88 g of sodium acetate trihydrate in 140 ml of water.

The formaldoxime solution was transferred to a 12 l. flask containing 26 g (0.10 mole) of cupric sulfate pentahydrate, 4 g (0.03 mole) of sodium sulfite and 640 g (4.7 moles) of sodium acetate trihydrate in 720 ml of water. The diazonium salt solution was introduced below the surface of the solution with stirring over 25 minutes at 10°–15°. Stirring was continued in the cold for one hour before allowing the reaction to warm to room temperature over 18 hours. The mixture was acidified with 920 ml of conc. hydrochloric acid, heated at reflux for 2 hours and steam-distilled until the distillate was clear. The combined distillates were saturated with solid sodium chloride and extracted with three portions of ether. The combined ethereal extracts were washed with four portions each of saturated sodium chloride, 5% sodium bicarbonate, saturated sodium chloride, and concentrated in vacuo to give 75 g of orange oil. This oil was treated with 100 ml of a warm (60°) solution of 40% aqueous sodium metabisulfite with occasional shaking over one hour. The mixture was diluted with 200 ml of ether, filtered, and the solid slurried in fresh ether and collected to give 90 g of lustrous white flakes, mp 162°–5° (dec.). This bisulfite adduct was heated in 600 ml of 20% sulfuric acid on the steam-bath for two hours. The cooled mixture was saturated with salt and extracted with three portions of ether. The combined organic layers were washed with three portions of 5% bicarbonate and three portions of brine. This ether solution was dried, concentrated in vacuo and pumped free of solvent to give 42 g of pale orange oil which is sufficiently pure for further reaction. The m-methylthiobenzaldehyde can be vacuum distilled at 103°–107° 1.5 mm Hg if necessary.

A suspension of 12.0 g (0.25 mole) of 50% sodium hydride/mineral oil in 175 ml of dry dimethylsulfoxide was heated at 65–70° for three hours under nitrogen. The dark green solution was diluted with 175 ml of tetrahydrofuran, cooled to 0° and treated with a solution of 50.9 g (0.25 mole) of trimethylsulfonium iodide in 175 ml of dry dimethylsulfoxide drop-wise at 0°–3° over 6 minutes. After an additional minute a solution of 21.0 g (0.14 mole) of m-methylthiobenzaldehyde in 10 ml of dry dimethylsulfoxide was added drop-wise at 0°–6° over 5 minutes.

The reaction was stirred at 0° for 15 minutes and then allowed to warm to room temperature over 1½ hours. The reaction was quenched on 2½ l. of ice and pH 7 buffer, extracted with three 600 ml portions of 1:1 benzene-ether, the combined organic layers washed once with 400 ml of water and dried over sodium sulfate. This solution was concentrated in vacuo (<40°) and pumped free of solvent to give 18 g of pale yellow m-methylthiostyrene oxide sufficiently pure by tlc and (i.r.) for further reaction.

A mixture of 18 g (0.108 mole) of m-methylthiostyrene oxide and 19.6 g (0.108 mole) of homoveratrylamine was heated at 100°–105° for 24 hours under nitrogen. The reaction was cooled to 50° and diluted with 50 ml of ethyl acetate. The solution was cooled, seeded and refrigerated overnight. The white precipitate was filtered, washed with cold ether and air-dried to give 13.6 g of white powder; α-[N-3,4-dimethoxyphenethyl)aminomethyl]-3′-methylthiobenzyl alcohol, mp 83.5°–84.5°.

A solution of 12.8 g (36.8 mmoles) of the alcohol in 130 ml of 48% hydrobromic acid was heated at 100°–102° for 5 hours under nitrogen. The reaction was diluted with 520 ml of water and heated on the steam-bath for 2 hours. (If the latter step is eliminated the product will be contaminated with a considerable amount of dimethyl sulfonium salt). This solution was treated with decolorizing charcoal, concentrated in vacuo, the residue twice redissolved in water and reconcentrated and finally diluted to 350 cc with water and refrigerated for two days. The precipitate was collected and oven-dried to give 9.2 g of cream-colored hydrobromide salt of 7,8-dihydroxy-1-(m-methylthiophenyl)-2,3,4,5-tetrahydro-1H-3-benzazepine, mp 155° (dec.) which showed ¼ mole of water of hydration upon analysis.

The base is generated by shaking in ethyl acetate/carbonate, separating the organic layer and evaporating the dried organic layer.

EXAMPLE 5

A solution of 8.5 g (22 mmoles) of 7,8-dihydroxy-1-(m-methylthiophenyl)-2,3,4,5-tetrahydro-1H-3-benzazepine hydrobromide, hydrate in 35 ml of dry pyridine at 5° was treated with 17 ml of acetic anhydride and stirred at room temperature for 20 hours. The reaction was quenched on 1.2 l. of ice-water and the gum-like precipitate collected by filtration while cold. The filter cake was taken up in 170 ml of ethyl acetate, washed with 2 × 25 ml portions of 1N hydrochloride acid, 2 × 25 ml portions of 5% bicarbonate and 1 × 25 ml portion of saturated sodium chloride. The organic layer was dried, concentrated in vacuo and pumped free of solvent to give 9.0 g of orange syrup, 7,8-diacetoxy-1-diacetoxy-1-(m-methylthiophenyl)-2,3,4,5-tetrahydro-1H-3-benzazepine acetamide, which was sufficiently pure by thin-layer chromatography and nmr for further use.

EXAMPLE 6

A solution of 8.6 g (20 mmoles) of 7,8-diacetoxy-1-(m-methylthiophenyl)-2,3,4,5-tetrahydro-1H-3-benzazepine acetamide in 40 ml of reagent grade methanol at −5° was treated with 40 ml of 0.52M sodium periodate (20.8 mmoles) drop-wise over 15 minutes at 0°. The mixture was refrigerated for 18 hours, filtered and the filter-cake washed with 2 × 83 ml, 2 × 12 ml portions of chloroform, air-dried to give 3.9 g of sodium iodate. The filtrate was separated, the aqueous layer extracted once with 35 ml of chloroform and the combined organic layers dried over magnesium sulfate. The solution was concentrated in vacuo and pumped free of solvent to give 8.9 g of yellow foam.

A solution of 709 mg (1.66 mmoles) of this foam in 4 ml of ethanol and 7 ml of 3N hydrochloric acid was refluxed for 4 days under nitrogen. The reaction was concentrated in vacuo, the residual red syrup taken up in 2½ ml of water, made alkaline with conc. ammonium hydroxide and extracted several times with ethyl acetate. The extracts were evaporated to dryness, redissolved in ethyl/acetate and reconcentrated several times and then treated with ethereal hydrogen chloride. The white precipitate was collected after trituration with fresh ether and dried over phosphorus pentoxide at 78° in vacuo to give 65 mg of white powder; 7,8-dihydroxy-1-(m-methylsulfinylphenyl)-2,3,4,5-tetrahydro-1H-3-benzazepine, hydrochloride, m.p. ~161° (dec) which showed ¾ mole of water of hydration upon analysis.

EXAMPLE 7

A solution of 7.10 g (18.6 mmoles) of 7,8-dihydroxy-1-(m-methylthiophenyl)-2,3,4,5-tetrahydro-1H-3-benzazepine hydrobromide in 120 ml of aqueous dimethylformamide at 0° under an argon atmosphere was basified to pH 10.0 with 10% sodium hydroxide solution. To this cold mixture was added 13.0 g (76 mmoles) of carbobenzoxy chloride in small portions over 15 minutes with concomitant addition of 10% alkali so as to maintain a pH of 10 to 10.5. The reaction was allowed to warm to room temperature after stirring at 0° for 1½ hours. The mixture was diluted with brine extracted with three portions of ethyl acetate. The combined organic extract was back-washed twice with brine. The dried extract was concentrated in vacuo and heated at 75°/0.1 mmHg to remove benzyl alcohol. The weight of the residual syrup base as 12.5 g.

This syrup was taken up in 50 ml of glacial acetic acid, cooled to 15° and treated with 14 ml of 40% peracetic acid over 5 minutes at 10°–15°. The solution was allowed to warm to room temperature when an aliquot was removed and subjected to analysis. This indicated that conversion was incomplete. Three treatments with 18, 10 and 5 ml portions of 40% peracetic acid were necessary to effect complete conversion to the sulfone. The reaction was quenched in 800 ml of water and extracted with three portions of ethyl acetate. The combined organic layers were washed with two portions of brine, three portions of 5% bicarbonate and two portions of brine. The extracts were dried, treated with decolorizing charcoal, concentrated in vacuo and pumped free of solvent to give 12 g of syrup.

This protected sulfone was treated with 70 ml of 38% hydrobromic acid in glacial acetic acid at room temperature for 1½ hours. The solution was added dropwise into 1 l. of rapidly stirred anhydrous diethyl ether over 40 minutes. The solids were allowed to settle and the supernatant was decanted. The precipitate was washed several times with fresh ether and dried under a nitrogen stream to give 5.4 g of the hydrobromide salt. To a solution of this salt in 150 ml of water was added 600 ml of ethyl acetate and the mixture was made basic with conc. ammonium hydroxide to pH 8.5. The organic phase was separated. The aqueous phase was saturated with salt and extracted three times with ethyl acetate. The combined organic layers were back-washed once with brine, dried and evaporated to dryness in vacuo to give 4.5 g of free base. This solid was taken up in 50 ml of methanol, treated with ethereal hydrogen chloride and added slowly to 350 ml of rapidly stirred anhydrous ethyl ether. The precipitate was slurried with fresh ether after decantation, filtered under nitrogen and dried in vacuo at 100° for 18 hours to give 4.0 g of white hydrochloride salt which softens at ca. 170°, melts >250°; 7,8-dihydroxy-1-(m-methylsulfonylphenyl)-2,3,4,5-tetrahydro-1H-3-benzazepine hydrochloride.

EXAMPLE 8 o-Methylthiobenzaldoxime was prepared from formaldoxime and 0.9 mole of o-methylthioaniline in the same manner as that described above for the meta-isomer. This oxime was refluxed for 3 hours in 820 ml of conc. hydrochloric acid and steam-distilled. The distillate was saturated with solid salt and extracted with three portions of diethyl ether. The combined ether extracts were washed with four portions of 5% bicarbonate and four portions of brine. The extract was dried and concentrated in vacuo to give 65 g of oil whose infrared spectrum showed a large nitrile band and a relatively small carbonyl absorption. The major component of this mixture was separated by column chromatography (silica gel, 1:2 diethyl ether-petroleum ether) and crystallized from petroleum ether) and crystallized from petroleum ether to give 40 g of white needles, mp 33°–35°. This material was identical with authentic o-methylthiobenzonitrile.

A mixture of 40 g (0.268 mole) of o-methylthiobenzonitrile, 40 g of 1:1 nickel-aluminum powder and 600 ml of 75% formic acid was cautiously heated to reflux over 30 minutes. Refluxing was continued for 2½ hours. The reaction mixture was cooled, filtered and washed with ethanol. The filtrate was concentrated in vacuo to ca. 200 cc, diluted with 1½ l. of water and extracted with four portions of chloroform. The combined organic extract was washed once with water, once with 5% bicarbonate and concentrated in vacuo to give about 50 g of syrup. This syrup was treated with 300 ml of warm (60%) 40% sodium metabisulfite solution for 20 minutes with occasional shaking. The white crystalline mass was collected, washed well with diethyl ether and air-dried to give 38.3 g of bisulfite adduct m.p. 83°–5°. The filtrate, which contained unreacted nitrile, was separated and the ether layer was combined with an ether extract of the aqueous phase. The organic extract was dried and concentrated in vacuo to give 10 g of recovered starting material. This was treated with 10 g of nickel aluminum as above and an additional 4.5 g of bisulfite adduct was collected. A solution of 42.8 g of this adduct in 240 ml of 17% sulfuric acid was heated on the steam-bath for 2¼ hours. The reaction mixture was cooled, saturated with solid salt and extracted with three portions of ether. The combined extracts were washed with 5% bicarbonate and brine, dried, concentrated in vacuo and pumped free of solvent to give 20 g of o-methylthiobenzaldehyde.

A mixture of 11 g (0.26 mole) of 57% sodium hydride and 183 ml of dry dimethyl sulfoxide was heated at 61°–66° for 2 hours under dry nitrogen. The dark-green solution was diluted with 183 ml of dry tetrahydrofuran and cooled to −3°. A solution of 53.5 g (0.26 mole) of trimethylsulfonium iodide in 183 ml of dry dimethylsulfoxide was added drop-wise over 12 minutes at −3° to +2° to the dimsyl anion solution. After 5 minutes a solution of 19.2 g (0.126 mole) of o-methylthiobenzaldehyde in 20 ml of dry dimethyl sulfoxide was added drop-wise over 10 minutes at 0°–6°. The reaction was allowed to warm slowly to room temperature after stirring for 30 minutes in the cold. The mixture was quenched on 2½ l. of ice water and extracted with three 300 ml. portions of 1:1 benzene-ether. The combined organic extracts were back-washed twice with water, dried over magnesium sulfate and concentrated in vacuo to give 20 g of oil, o-methylthiostyrene oxide, which did not have a carbonyl band in its infrared spectrum. This oil was used immediately.

A mixture of 20 g (0.12 mole) of o-methylthiostyrene oxide and 22.8 g (0.126 mole) of homoveratrylamine was heated at 110° for 2 hours under nitrogen. The solid reaction mixture was dissolved in 650 ml of hot methanol and allowed to crystallize slowly over 18 hours in the refrigerator. The crystals were filtered, washed with diethyl ether and air-dried to give 20 g of product m.p. 140°–142°; α-[N-(3,4-dimethoxyphenethyl)aminomethyl]-2′-methylthiobenzyl alcohol.

A solution of 19 g (54.7 mmoles) of α-[N-(3,4-dimethoxyphenethyl)aminomethyl]-2′-methylthiobenzyl alcohol in 150 ml of 48% hydrobromic acid was heated at 125° for 3½ hours under nitrogen. The reaction mixture was cooled in an ice-bath, filtered and air-dried to give 23.5 g of tan powder. Crystallization from 200 ml of hot water and treatment with decolorizing charcoal gave 16.5 of short needles mp 152° (shrinking) to 175° after drying at 56°/0.1 mm Hg for 7 hours. This material, 7,8-dihydroxy-1-(o-methylthiophenyl)-2,3,4,5-tetrahydro-1H-3-benzazepine, hydrobromide, hydrate, shows the presence of ¾ mole of water of hydration on analysis.

EXAMPLE 9

The catechol from Example 1 (1.0 g, 2.4 mmole) was slurried in 15 ml of trifluoroacetic acid while 0.39 ml (5.28 mmole) of acetyl bromide in 5 ml of trifluoroacetic acid was added. After stirring at room temperature for 3½ hours and heating at reflux for 1 hour, analysis by t.l.c. (20% methanol/chloroform) showed reaction was incomplete. An additional 0.4ml of acetyl bromide was added following a reflux period of 2 hours then standing overnight at room temperature. The reaction mixture was concentrated to dryness. The residue was taken up in toluene and concentrated. The residue was passed over silica gel in chloroform → 5% methanol/chloroform to give 0.47 g (39%) of 6-chloro-7,8-diacetoxy-1-(p-methylthiophenyl)-2,3,4,5-tetrahydro-1H-3-benzazepine hydrobromide.

EXAMPLE 10

A 4 g sample of 7,8-dihydroxy-1-(p-methylthiophenyl)-2,3,4,5-tetrahydro-1H-3-benzazepine is slurred in 25 ml of acetone and 0.8 g (~10% excess) of ethylene oxide is added. The mixture is placed in a pressure bottle and stirred at ambient temperature for about 40 hours. The reaction mixture is then heated to 60°–80° for 30 minutes, cooled and filtered. Concentration of the filtrate gives a solid which is taken up in ethyl acetate and reprecipitated with ether. The solid thus obtained is dissolved in ethanol and treated with ethereal hydrogen chloride to give 7,8-dihydroxy-3-(2-hydroxyethyl)-1-(p-methylthiophenyl)-2,3,4,5-tetrahydro-1H-3-benzazepine hydrochloride.

EXAMPLE 11

A solution of 4 g of 6-chloro-7,8-dimethoxy-1-(p-methylthiophenyl)-2,3,4,5-tetrahydro-1H-3-benzazepine in 15 ml of formic acid and 10 ml of formaldehyde is refluxed for 18 hours. The reaction mixture is evaporated to dryness, 20 ml of 6N hydrochloric acid is added and the solution is again evaporated to dryness to give a liquid. The latter is treated with 20 ml of 10% sodium hydroxide solution and the mixture is extracted with ether. The dried extract is evaporated to give 6-chloro-7,8-dimethoxy-3-methyl-1-(p-methylthiophenyl)-2,3,4,5-tetrahydro-1H-3-benzazepine.

The above prepared N-methyl benzazepine (2.6 g) is dissolved in 120 ml of dry methylene chloride and 6.8 g (0.027 mol) of boron tribromide is added dropwise at −10°. The resulting solution is warmed to room temperature and stirred for two hours. Working up the reaction as disclosed above gives 6-chloro-7,8-dihydroxy-3-methyl-1-(p-methylthiophenyl)-2,3,4,5-tetrahydro-1H-3-benzazepine hydrobromide.

EXAMPLE 12

Substituting a stoichiometric quantity of 2-fluoro-3,4-dimethoxyphenethylamine in the synthetic procedures of Example 1 gives 6-fluoro-7,8-dimethoxy-1-(p-methylthiophenyl)-2,3,4,5-tetrahydro-1H-3-benzazepine. Hydrolysis with boron tribromide as disclosed above gives 6-fluoro-7,8-dihydroxy-1-(p-methylthiophenyl)-2,3,4,5-tetrahydro-1H-3-benzazepine. Substituting 2-trifluoromethyl-3,4,-dimethoxyphenethylamine, prepared via 2-trifluoromethyl-3,4,-dimethoxytoluene, in Example 1 gives 6-trifluoromethyl-7,8-dimethoxy-1-(p-methylthiophenyl)-2,3,4,5-tetrahydro-1H-3-benzazepine and hydrolysis with boron tribromide gives 6-trifluoromethyl-7,8-dihydroxy-1-(p-methylthiophenyl)-2,3,4,5-tetrahydro-1H-3-benzazepine.

Likewise other phenethylamines can be substituted such as 3,4-dibutoxyphenethylamine, 3,4-methylene or ethylenedioxyphenethylamine or their 2-chloro congeners to give 7,8-dibutoxy or 3,4-methylenedioxy-1-(p-methylthiophenyl)-2,3,4,5-tetrahydro-1H-3-benzazepines or their 6-chloro congeners.

Substituting the secondary phenethylamines of U.S. 3,393,192 in the process of Example 1 gives 3-allyl-7,8-dihydroxy-1-(p-methylthiophenyl)-2,3,4,5-tetrahydro-1H-3-benzazepine, 3-n-butyl-7,8-dihydroxy-1-(p-methylthiophenyl)-2,3,4,5-tetrahydro-1H-3-benzazepine-3-(3',3'-dimethylallyl-7,8-dihydroxy-1-(p-methylthiophenyl)-2,3,4,5-tetrahydro-1H-3-benzazepine or 3-benzyl-7,8-dihydroxy-1-(p-methylthiophenyl)-2,3,4,5-tetrahydro-1H-3-benzazepine.

EXAMPLE 13

7,8-Dimethoxy-1-(p-methylthiophenyl)-2,3,4,5-tetrahydro-1H-3-benzazepine (5 g) is suspended in benzene and an excess of trifluoroacetic anhydride is added in the presence of a scavenger amine. The solution is stirred at room temperature then stripped to leave the desired N-trifluoroacetyl derivative. Other lower alkanoyl chlorides or anhydrides may be reacted similarly.

EXAMPLE 14

To a suspension of 7.0 g of 7,8-dihydroxy-1-(p-methylthiophenyl)-2,3,4,5-tetrahydro-1H-3-benzazepine hydrobromide in 100 ml of trifluoroacetic acid was added cautiously at room temperature 25 ml of acetyl bromide. In a short time all the solid went into solution and after stirring for an additional hour at room temperature the solvents were evaporated to a syrupy residue. Trituration with ether gave just slightly tacky hydrobromide salt of the O-diacetyl derivative. This product was homogeneous on tlc (9:1 chloroform/methanol) and was used as is for the next reaction by quickly dissolving in dry pyridine (100 ml) and cooling the solution in ice/water. Excess benzyl chloroformate (15 ml) was added dropwise. After being stirred at 0° for ½ hour and for 3 hours at 25° the reaction mixture was poured into a large volume of ice/water, extracted well with ethyl acetate and washed with dilute acid, water, base and brine solution. The dried solution was concentrated to a foam. The nmr was consistent with the desired O-diacetate N-carbobenzoxy derivative and the tlc was homogeneous (1:1 ethyl acetate-cyclohexane on silica).

To an ice cold solution of 8.0 g of the carbobenzoxy derivative in 200 ml of methanol was added dropwise 32 ml of 0.5M sodium periodate. After about ½ hour the cooling bath was removed and the mixture was stirred at room temperature overnight as sodium iodate precipitated. The reaction was diluted with a large volume of water and extracted well with ethyl acetate. After a water wash the dried solution was concentrated to a yellow syrup which was chromatographed over Brinkman "60" silica gel with an ethyl acetate/cyclohexane gradient. The sulfoxide was eluted mostly with 5:1 ethyl acetate-cyclohexane to give the pale yellow, syrupy sulfoxide. A field desorption mass spectrum showed the correct molecular ion (535) and the nmr was consistent with structure.

In 80 ml of trifluoroacetic acid was dissolved 1.0 g of the N-carbobenzoxy sulfoxide and the solution was stirred at 55°–60° for 17 hours. The solvent was evaporated to the residual trifluoro acetate salt. A few drops of 3N hydrochloric acid was added to the residue and it was immediately evaporated at a high vacuum at room temperature to give the nearly white hydrochloride salt, mp 125°–130°, of 7,8-diacetoxy-1-(p-methylsulfoxyphenyl)-2,3,4,5-tetrahydro-1H-3-benzazepine, hydrochloride, hydrate.

In 250 ml of 3N hydrochloric acid and 100 ml of dimethoxyethane was dissolved 1.25 g of the O-diocetyl-N-carbobenzoxy sulfoxide intermediate. The solution was stirred under nitrogen at 95° (oil bath temperature) for 4 hours, evaporated to ½ the volume and chilled. The solid was collected and washed well with ether to give 720 mg of 7,8-dihydroxy-1-(p-methylsulfoxyphenyl)-2,3,4,5-tetrahydro-1H-3-benzazepine, hydrochloride, hydrate, mp 155°–160°.

EXAMPLE 15

To an ice cold solution of 764 mg (2 mmole) of 7,8-dihydroxy-1-(p-thiomethylphenyl)-2,3,4,5-tetrahydro-1H-3-benzazepine, hydrobromide in 15 ml of methanol (under nitrogen) was added all at once 554 mg (2.4 mmole) of 2,3-dichloro-5,6-dicyano-1,4-benzoquinone (DDQ). A reddish solid appeared in a short time. The suspension was stirred about 30 minutes in the cold, the reddish solid was filtered, washed with a little cold methanol and air dried to give the maroon solid (607 mg, 80%) 7,8-o-quinone derivative of the starting material.

A suspension of 200 mg of the above quinone in 10 ml of acetic acid was partially cooled in ice. Then 5 ml of a saturated solution of dry hydrogen bromide in acetic acid was added all at once. The mixture began to lighten from reddish to a pale yellow as the temperature was allowed to rise to 25°. After 15 additional minutes, excess ether was added and the white highly crystalline produce filtered. A mass spectrum showed the product to be a mixture of the starting catechol and 6-monobrominated product which is separated by isolation methods known to the art.

Another method to introduce a bromide atom exclusively at the 6-position of 1-phenylbenzazepines involves in situo oxidation of the catechol with a current of 0.6–0.7 volts in a dilute HBr solution in a cyclic voltammetric or constant current apparatus. The 7,8-dione generated in situ is brominated at ambient temperature in 2–4 hours.

EXAMPLE 16 p-Trifluoromethylthiobenzaldehyde (14.8 g, 0.072 mole) was converted to the styrene oxide derivative as described above using 4.8 g (0.1 mole) of 50% sodium hydride in 80 ml of dimethyl sulfoxide and 20.4 g (0.1 mole) of trimethyl sulfonium iodide. The crude p-trifluoromethylthio styrene oxide (12.5 g, 79%) was consistent with the IR and nmr spectra. This was used crude for the reaction with homoveratrylamine. The epoxide (12 g, 0.055 mole) and 11.8 g (0.065 mole) of homoveratrylamine was stirred under nitrogen in an oil bath at 95°–100° for 4½ hours. The product was chromatographed over silica gel using a 6–20% methanol in chloroform gradient. The 4-trifluoromethylthio-α-[N-(3,4-dimethoxyphenethyl)aminomethyl]-benzyl alcohol (10 g, 69%) had mp 99°–101°.

The amino alcohol 10 g (0.027 mole) was dissolved in 80 ml of trifluoroacetic acid and 2.1 ml of conc. sulfuric acid and refluxed for 1½ hours. The solution was evaporated to dryness, the residue made basic with ammonia solution and the free base of the benzazepine was extracted into ethyl acetate. The dried, concentrated solution gave a viscous brown residue of 7,8-dimethoxy-1-(p-trifluoromethylthiophenyl)-2,3,4,5-tetrahydro-1H-3-benzazepine (6.0 g, 63%). This product was demethylated without further purification.

In 80 ml of dry methylene dichloride was dissolved 6.0 g of the above dimethoxybenzazepine. The solution (under nitrogen) was cooled to −10° and 13 g of boron tribromide was added dropwise. Then the mixture was stirred at room temperature for 3 hours, recooled in ice and excess methanol was added. The solution was concentrated in vacuo and the residue chromatographed over silica gel in a methanol/chloroform gradient. The homogeneous fractions were dissolved in acetone, and precipitation with ether gave 2.7 g, mp ~95°, of 7,8-dihydroxy-1-(p-trifluoromethylthiophenyl)-2,3,4,5-tetrahydro-1H-3-benzazepine hydrobromide.

Substituting an equivalent amount of 2-(2-chloro-3,4-dimethoxyphenyl)ethylamine from Example 1 in the above procedure gives 7,8-dihydroxy-6-chloro-1-(p-trifluoromethylthiophenyl)-2,3,4,5-tetrahydro-1H-3-benzazepine hydrobromide.

EXAMPLE 17

The Princeton Applied Research Model 193 Digital Coulometer was used for the controlled potential electrolysis. The electrolysis cell was a three-electrode system. A platinum gauge working electrode (anode), a saturated calomel reference electrode and an auxiliary electrode (cathode) which was separated from the solution by a vycor frit. Supporting electrolyte - 0.5M hydrobromic acid.

1.0 q. of 1-(p-methylthiophenyl-7,8-dihydroxy-2,3,4,5-tetrahydro-1H-3-benzazepine hydrobromide was dissolved in 50 ml of 0.5 M hydrobromic acid solution by warming on a steam bath for one hour and then poured into the electrolytic cell. After purging with nitrogen gas for 10 minutes, the electrolysis was conducted at 0.7 vs. SCF. The initial light yellow solution turned to reddish brown and then to dark brown after 5 minutes and the electrolysis slowed down. 2.8 ml of 48% hydrobromic acid was added and the electrolysis was completed in 4 hours as indicated by t.l.c. over silica (ethyl acetate-methanol-ammonium hydroxide 75:23:2). New product had an $R_f$= 0.6 compared to the starting material with $R_f$ = 0.5. The resultant dark brown solution was evaporated to complete dryness in vacuo to give tan gummy solid crude product which was recrystallized from methanol-ethyl acetate. Tan solid product was collected and dried. Wt. 0.65 g, yield 54%. It was characterized by nmr, t.l.c. or mass spect. as 6-bromo-7,8-dihydroxy-1(p-methylthiophenyl)-2,3,4,5-tetrahydro-1H-3-benzazepine hydrobromide.

Other adducts may be also be used in this procedure such as hydrogen chloride.

EXAMPLE 18

| Ingredients | Mg. per Capsule |
|---|---|
| 6-Chloro-7,8-dihydroxy-1-(p-methyl-thiophenyl)-2,3,4,5-tetrahydro-1H-3-benzazepine (as an acid addition salt) | 200 (free base) |
| Magnesium stearate | 2 |
| Lactose | 200 |

The above ingredients are thoroughly mixed and placed into hard gelatin capsules. Such capsules are administered orally to subjects in need of treatment from 1–5 times daily to induce peripheral dopaminergic activity.

EXAMPLE 19

| Ingredients | Mg. per Tablet |
|---|---|
| 7,8-Dihydroxy-1-(p-methylthiophenyl)-2,3,4,5-tetrahydro-1H-3-benzazepine (as an acid addition salt) | 200 (free base) |
| Corn starch | 30 |
| Polyvinyl pyrrolidone | 12 |
| Corn starch | 16 |
| Mangesium stearate | 3 |

The first two ingredients are thoroughly mixed and granulated. The granules obtained are dried, mixed with the remaining corn starch and magnesium stearate, and compressed into tablets.

The capsules or tablets thusly prepared are administered orally to an animal or human requiring stimulation or peripheral dopamine receptors within the dose ranges set forth hereinabove. The end result is a diuretic and/or hypotensive activity. Similarly other compounds of Formula I and the illustrative examples can be formulated in the same manner to give pharmaceutical compositions useful in the methods of this invention based on the chemical characteristics and relative biological activity using the test methods outlined.

What is claimed is:

1. A chemical compound of the structural formula:

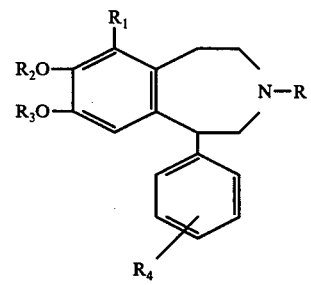

in which:
R is hydrogen, benzyl, phenethyl, carbobenzoxy, hydroxyethyl, lower alkyl of 1–5 carbons, lower alkenyl of 3–5 carbons or lower alkanoyl of 1–5 carbons;
$R_1$ is hydrogen, halo or trifluoromethyl;
$R_2$ and $R_3$ are each hydrogen, lower alkyl of 1–5 carbons, lower alkanoyl of 2–5 carbons or, when taken together, methylene and ethylene; and
$R_4$ is lower alkylthio of 1–5 carbons, lower alkylsulfinyl of 1–5 carbons, lower alkylsulfonyl of 1–5 carbons, trifluoromethylthio, trifluoromethylsulfonyl, trifluoromethylsulfinyl, or dimethylsulfonium halide; or a nontoxic, pharmaceutically acceptable salt thereof.

2. The chemical compound of claim 1 in which $R_2$ and $R_3$ are hydrogen.

3. The chemical compound of claim 1 in which R is hydrogen or methyl.

4. The chemical compound of claim 3 in which $R_4$ is p-methylthio, m-methylsulfonyl or p-dimethylsulfonium bromide.

5. The chemical compound of claim 2 in which $R_1$ is chloro.

6. The chemical compound of claim 2 in which $R_1$ is chloro and $R_4$ is p-methylthio, m-methylsulfonyl or p-dimethyl sulfonium bromide.

7. The compound of claim 1 being 6-chloro-7,8-dihydroxy-1-(p-methylthiophenyl)-2,3,4,5-tetrahydro-1H-3-benzazepine or its nontoxic pharmaceutically acceptable acid addition salts.

8. The compound of claim 7 in the form of the free base.

9. The compound of claim 7 in the form of the hydrobromide or hydrochloride salt.

10. The compound of claim 1 being 7,8-dihydroxy-1-(p-methylthiophenyl)-2,3,4,5-tetrahydro-1H-3-benzazepine.

11. The compound of claim 1 being 7,8-dihydroxy-1-(p-dimethylsulfoniumphenyl)-2,3,4,5-tetrahydro-1H-3-benzazepine or its nontoxic, pharmaceutically acceptable salts.

12. The compound of claim 1 being 7,8-dihydroxy-1-(m-methylsulfonylphenyl)-2,3,4,5-tetrahydro-1H-3-benzazepine or its nontoxic pharmaceutically acceptable salts.

13. The compound of claim 1 being 7,8-diacetoxy-6-chloro-1-(p-methylthiophenyl)-2,3,4,5-tetrahydro-1H-3-benzazepine or its nontoxic pharmaceutically acceptable salts.

14. The compound of claim 1 being 7,8-dihydroxy-7-chloro-3-methyl- 1-(p-methylthiophenyl)-2,3,4,5-tetrahydro-1H-3-benzazepine or its nontoxic pharmaceutically acceptable salts.

15. The method of inducing dopaminergic activity in a subject in need thereof comprising administering orally or by injection a nontoxic dopaminergic quantity of a compound of claim 1.

16. A pharmaceutical composition comprising a nontoxic dopaminergic quantity of a compound of claim 1 combined with a pharmaceutical carrier.

* * * * *